United States Patent
Bulick et al.

(10) Patent No.: US 10,246,474 B2
(45) Date of Patent: Apr. 2, 2019

(54) PREPARATION OF A HYDROXYALKYL PHOSPHONIC ACID

(71) Applicant: Rohm and Haas Company, Philadelphia, PA (US)

(72) Inventors: Allen S. Bulick, East Norriton, PA (US); Sarah L. Hruby, North Wales, PA (US); Muhunthan Sathiosatham, Chalfont, PA (US)

(73) Assignee: Rohm and Haas Company, Philadelphia, PA (US)

( * ) Notice: Subject to any disclaimer, the term of this patent is extended or adjusted under 35 U.S.C. 154(b) by 544 days.

(21) Appl. No.: 14/733,016

(22) Filed: Jun. 8, 2015

(65) Prior Publication Data

US 2015/0361117 A1 Dec. 17, 2015

Related U.S. Application Data

(60) Provisional application No. 62/012,489, filed on Jun. 16, 2014.

(51) Int. Cl.
*C07F 9/38* (2006.01)

(52) U.S. Cl.
CPC .................. *C07F 9/3808* (2013.01)

(58) Field of Classification Search
CPC .................................. C07F 9/3808
See application file for complete search history.

(56) References Cited

U.S. PATENT DOCUMENTS

| 4,069,245 A | 1/1978 | Dursch et al. |
| 4,069,247 A | 1/1978 | Kleiner |

FOREIGN PATENT DOCUMENTS

| DE | 2313355 A1 | 9/1974 | |
| DE | 2745982 | * 4/1979 | ............... C07F 9/30 |
| WO | 2009029062 A1 | 3/2009 | |

OTHER PUBLICATIONS

Schumann et al. (Zur Chemie Der 2-hydroxyethanphosphonsaure, Phosphorus and Sulfur and the Related Elemnts, vol. 13, Issue 3, , pp. 363-370, 1982).*
Dow (Dowex Ion Exchange Resins, Powerful Chemical Processing Tools, 12 pages, Jun. 2002).*
Hammerschmidt (Incorporation of I[Methyl-2H3]methionine and 2-[Hydroxy-18O]hydroxyethylphosphonic Acid into Fosfomycin in Streptomyces fradiae and unusual methyl transfer, Angew. Chem. Int. Ed. Engl, 1994, pp. 341-342, vol. 33, No. 3).*
Schumann et al. (Zur Chemie Der 2-hydroxyethanphosphonsaure, Phosphorus and Sulfur and the Related Elements, vol. 13, Issue 3, pp. 363-370, 1982).*
Hydrolytically Stable Acidic Monomers Used in Two Steps Self-Etch Adhesives, Derbanne et al, Polymer Degradation and Stability 98, 2013 pp. 1688-1698.
Search report from corresponding Chinese 201510303240.3 application, dated Mar. 27, 2018.
H J Kleiner. et al "Zur Chemie Der 2-Hydroxyethanp Hosphonsaure, Phosphorus and Sulfur" vol. 13, Dec. 31, 1982, p. 364.

* cited by examiner

*Primary Examiner* — Rosalynd A Keys
(74) *Attorney, Agent, or Firm* — Reid S. Willis

(57) ABSTRACT

The present invention is a process for converting a phosphonate to a hydroxyalkyl phosphonic acid comprising the step of contacting together water, the phosphonate, and a sulfonated or phosphonated heterogeneous catalyst under conditions sufficient to convert at least 50% of the phosphonate to the hydroxyalkyl phosphonic acid. The process of the present invention provides a way of preparing hydroxyalkyl phosphonic acids safely and economically, without corrosive effects.

4 Claims, No Drawings

PREPARATION OF A HYDROXYALKYL PHOSPHONIC ACID

BACKGROUND OF THE INVENTION

The present invention relates to the preparation of a hydroxyalkyl phosphonic acid using an acid functionalized ion exchange resin.

The phosphonic acid monomer 2-(methacryloyloxy)alkyl phosphonic acid (MEP) is useful in the preparation of binders that adsorb to the surfaces of TiO$_2$ particles. Latexes functionalized with MEP have shown excellent heat age stability, hiding, and tint strength. MEP can be prepared by reacting hydroxyethyl phosphonic acid with methacrylic acid at a high temperature and sub-atmospheric pressure. The hydroxyethyl phosphonic acid is traditionally prepared by reacting the corresponding alkylphosphonate with a strong acid such as HCl. Unfortunately, this method is costly, corrosive, and toxic, resulting in the production of toxic alkyl chlorides such methyl chlorides as byproducts. It would therefore be desirable to find a safer and more economical process for preparing the hydroxyethyl phosphonic acid precursor to MEP.

SUMMARY OF THE INVENTION

The present invention addresses a need in the art by providing a process for converting a phosphonate, which is a hydroxyalkyl- or acyloxyalkyl-phosphonate, to a hydroxyalkyl phosphonic acid comprising the step of contacting together water, the phosphonate, and a sulfonated or phosphonated heterogeneous catalyst under conditions sufficient to convert at least 50% of the phosphonate to the hydroxyalkyl phosphonic acid.

DETAILED DESCRIPTION OF THE INVENTION

The present invention addresses a need in the art by providing a process for converting a phosphonate, which is a hydroxyalkyl- or acyloxyalkyl-phosphonate, to a hydroxyalkyl phosphonic acid comprising the step of contacting together water, the phosphonate, and a sulfonated or phosphonated heterogeneous catalyst under conditions sufficient to convert at least 50% of phosphonate to the hydroxyalkyl phosphonic acid.

Examples of suitable heterogeneous catalysts include crosslinked macroreticular ion exchange resins, and microporous aluminosilicate minerals (also known as zeolites). A commercial example of a suitable sulfonated ion exchange resin is AMBERLYST™-15 Ion Exchange Resin (a trademark of The Dow Chemical Company or its Affiliates).

The process is advantageously carried out at advanced temperatures, preferably at a temperature of from 80° C., more preferably from 90° C., to 120° C., more preferably to 110° C. and preferably for a period in the range of from 1 hour to 24 hours. An illustration of a preferred method for converting a hydroxyalkyl- or acyloxyalkyl-phosphonate to a hydroxyalkyl phosphonic acid is shown in Scheme 1.

Scheme 1

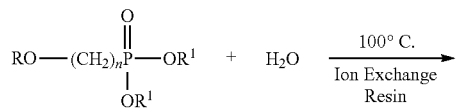

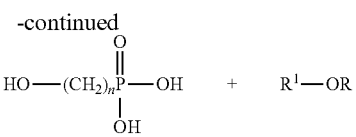

where R is H or acetyl; and R$^1$ is C$_1$-C$_{10}$-alkyl, preferably methyl, ethyl, propyl, isopropyl, or n-butyl; and n is 2 to 10, preferably 2 to 4. An example of a preferred hydroxyalkyl phosphonic ester is dimethyl-2-(acetyloxy)ethyl phosphonate; a preferred hydroxyalkyl phosphonic acid is 2-hydroxyethyl phosphonic acid.

In the case where the phosphonate is an acyloxyalkylphosphonate, the byproducts methyl acetate and methanol are advantageously removed during the course of the reaction by way of azeotropic distillation, which is believed to drive the reaction to completion more efficiently.

Preferably, at least 70% of the phosphonate is converted to the hydroxyalkyl phosphonic acid, more preferably at 85%.

EXAMPLE

A 500-mL four-neck round bottomed flask, equipped with a heating mantle, thermocouple, 10-tray Older-Shaw column, and distillation head was charged with dimethyl-2-(acetyloxy)ethyl phosphonate, (293 g, 1.5 mol), AMBERLYST-15 Ion Exchange Resin (48 g) and water (72 g, 4 mol). The resulting solution was heated to 100° C. After 15 h, the pot temperature was raised to 105° C. During this time vapor temperature often reached 95° C. and distillate contained primarily water. Approximately 150 g of additional water was added and volatile contents were removed in vacuo to yield 168 g (89%) of the hydroxyethyl phosphonic acid. The byproducts formed by the process of the present invention are methanol and methyl acetate, as compared to the corrosive and carcinogenic byproducts (hydrochloric acid and methyl chloride, respectively) that are formed by the traditional process that requires stoichiometric amounts of HCl as compared with catalytic amounts of the ion exchange resin. Yet another advantage of the process of the present invention is the flexibility to recycle and reuse the ion exchange resin.

The invention claimed is:

1. A process for converting a phosphonate to a hydroxyalkyl phosphonic acid comprising the step of contacting together water, the phosphonate, and a heterogeneous catalyst; wherein the heterogeneous catalyst is a sulfonated crosslinked macroreticular ion exchange resin; wherein the phosphonate is contacted with the sulfonated crosslinked ion-exchange resin at a temperature of from 80° C. to 120° C. for 1 to 24 hours to convert at least 70% of the phosphonate to the hydroxyalkyl phosphonic acid; wherein the phosphonate is characterized by the following formula:

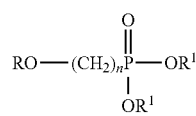

where R is H or acetyl; and R$^1$ is C$_1$-C$_{10}$-alkyl; and n is 2 to 10; and wherein methyl acetate and methanol are formed in addition to the hydroxyalkyl phosphonic acid.

2. The process of claim 1 wherein the methyl acetate and methanol are removed during the conversion of the phosphonate to the hydroxyalkyl phosphonic acid by way of azeotropic distillation.

3. The process of claim 2 wherein the phosphonate is dimethyl-2(acetyloxy)ethyl phosphonate, and the hydroxyalkyl phosphonic acid is 2hydroxyethyl phosphonic acid.

4. The process of claim 3 wherein the dimethyl-2(acetyloxy)ethyl phosphonate is contacted with the sulfonated ion-exchange resin at 90° C. to 110° C. for 1 to 24 hours to convert at least 85% of the dimethyl-2(acetyloxy)ethyl phosphonate to 2hydroxyethyl phosphonic acid.

* * * * *